(12) United States Patent
Yoshida et al.

(10) Patent No.: US 10,617,290 B2
(45) Date of Patent: Apr. 14, 2020

(54) LIGHT SOURCE APPARATUS FOR ENDOSCOPE HAVING FIRST SECOND AND THIRD HEAT SINKS FOR RESPECTIVE LIGHT SOURCES AND A FIRST AIR FLOW THROUGH THE FIRST AND THIRD HEAT SINKS AND A MERGED AIR FLOW THROUGH THE SECOND HEAT SINK

(71) Applicant: OLYMPUS CORPORATION, Tokyo (JP)

(72) Inventors: Yusuke Yoshida, Hachioji (JP); Masaaki Watanabe, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/140,802

(22) Filed: Sep. 25, 2018

(65) Prior Publication Data

US 2019/0021583 A1    Jan. 24, 2019

Related U.S. Application Data

(63) Continuation of application No. PCT/JP2017/010622, filed on Mar. 16, 2017.

(30) Foreign Application Priority Data

Apr. 27, 2016 (JP) ................... 2016-089639

(51) Int. Cl.
*A61B 1/12* (2006.01)
*F21V 29/503* (2015.01)
(Continued)

(52) U.S. Cl.
CPC ................ *A61B 1/128* (2013.01); *A61B 1/06* (2013.01); *A61B 1/0661* (2013.01); *F21S 2/00* (2013.01);
(Continued)

(58) Field of Classification Search
CPC ......... F21V 29/83; F21V 29/503; A61B 1/128
See application file for complete search history.

(56) References Cited

U.S. PATENT DOCUMENTS 7,384,151 B2 * 6/2008 Seki ....................... G03B 21/16
353/31
10,085,630 B2 * 10/2018 Shirota ................ A61B 1/0638
(Continued)

FOREIGN PATENT DOCUMENTS

EP        3090679 A1    11/2016
JP       S53-83371 A     7/1978
(Continued)

OTHER PUBLICATIONS

International Search Report dated May 16, 2017 issued in PCT/JP2017/010622.

*Primary Examiner* — Robert J May
(74) *Attorney, Agent, or Firm* — Scully, Scott, Murphy & Presser, P.C.

(57) ABSTRACT

A light source apparatus for endoscope includes: a housing including an intake port; a first heat radiating portion connected to a first light source and cooled by gas taken in from the intake port; a third heat radiating portion connected to a third light source, and cooled by gas taken in from the intake port; and a second heat radiating portion including a lower necessary cooling amount than the first heat radiating portion and the third heat radiating portion connected to a second light source provided in a flow path in which a flow path of the gas that passes through the first heat radiating portion and a flow path of the gas that passes through the third heat radiating portion are merged together, and cooled by merged gas merged on a merged flow path.

7 Claims, 4 Drawing Sheets

(51) Int. Cl.
*F21V 29/71* (2015.01)
*F21S 2/00* (2016.01)
*A61B 1/06* (2006.01)
*F21V 29/67* (2015.01)
*G02B 23/26* (2006.01)
*F21V 29/51* (2015.01)
*F21Y 113/13* (2016.01)
*F21Y 115/10* (2016.01)

(52) U.S. Cl.
CPC ............ *F21V 29/503* (2015.01); *F21V 29/51* (2015.01); *F21V 29/67* (2015.01); *F21V 29/673* (2015.01); *F21V 29/71* (2015.01); *G02B 23/26* (2013.01); *F21Y 2113/13* (2016.08); *F21Y 2115/10* (2016.08)

(56) References Cited

U.S. PATENT DOCUMENTS

| | | | |
|---|---|---|---|
| 10,092,174 B2 * | 10/2018 | Shirota | ............... G02B 23/24 |
| 2016/0353984 A1 | 12/2016 | Shirota et al. | |

FOREIGN PATENT DOCUMENTS

| | | |
|---|---|---|
| JP | 2001-267773 A | 9/2001 |
| JP | 2012-014992 A | 1/2012 |
| JP | 2014-045820 A | 3/2014 |
| JP | 2014-135350 A | 7/2014 |
| JP | 2014-211462 A | 11/2014 |
| WO | WO 2015/064470 A1 | 5/2015 |
| WO | WO 2015/178054 A1 | 11/2015 |

* cited by examiner

LIGHT SOURCE APPARATUS FOR ENDOSCOPE HAVING FIRST SECOND AND THIRD HEAT SINKS FOR RESPECTIVE LIGHT SOURCES AND A FIRST AIR FLOW THROUGH THE FIRST AND THIRD HEAT SINKS AND A MERGED AIR FLOW THROUGH THE SECOND HEAT SINK

CROSS REFERENCE TO RELATED APPLICATION

This application is a continuation application of PCT/JP2017/010622 filed on Mar. 16, 2017 and claims benefit of Japanese Application No. 2016-089639 filed in Japan on Apr. 27, 2016, the entire contents of which are incorporated herein by this reference.

BACKGROUND OF INVENTION

1. Field of the Invention

The present invention relates to a light source apparatus for endoscope configured to cool a plurality of heat-generating portions.

2. Description of the Related Art

Hitherto, endoscopes each configured to include an insertion portion having a shape of an elongated tube have been widely used in a medical field or an industrial field, for example. Among the endoscopes, a medical endoscope used in the medical field is configured to be able to observe an organ and the like by inserting the insertion portion in a subject such as a body cavity of a living body, or perform various types of treatment on the organ and the like with use of a treatment instrument inserted in a treatment instrument insertion channel included in the endoscope, as necessary. In addition, an industrial endoscope used in the industrial field is configured to be able to observe or inspect states of flaws or corrosion in an object, for example, apparatuses or machinery such as a jet engine or plant piping by inserting the insertion portion in the object.

In many cases, a target that is observed, for example, with use of the types of endoscopes as above is in a dark place such as a body cavity or the inside of an apparatus, and hence a light source apparatus configured to irradiate the target with illumination light is used. Solid-state light-emitting elements such as an LED (light emitting diode) or a laser light source are used in some light source apparatuses (hereinafter referred to as "light source apparatuses for endoscope") used in endoscopes in recent years. A plurality of solid-state light-emitting elements are provided in the types of light source apparatuses for endoscope as above so that illumination light having a desired color such as white light can be emitted.

In the light source apparatuses for endoscope as above, the calorific value of the respective solid-state light-emitting elements tends to increase because a large amount of illumination light needs to be emitted. Thus, in a conventional light source apparatus for endoscope, a cooling apparatus for cooling each solid-state light-emitting element serving as a heat source is included in a housing. The cooling apparatus in the conventional light source apparatus for endoscope is typically configured by components such as a cooling fan, a heat sink, and a heat pipe. The types of light source apparatuses for endoscope as above are proposed in International Publication No. WO2015/178054A1, International Publication No. WO2015/064470A1, and Japanese Patent Application Laid-Open Publication No. 2012-14992, for example, in various forms.

In the light source apparatuses for endoscope disclosed in International Publication No. WO2015/178054A1, International Publication No. WO2015/064470A1, Japanese Patent Application Laid-Open Publication No. 2012-14992, and the like, a flow path for cooling in a housing is divided into a plurality of flow paths.

On the other hand, in recent years, a light source apparatus for endoscope in which a larger number of solid-state light-emitting elements serving as light-emitting portions and heat sources are arranged has been proposed. Further, an apparatus including an even larger number of solid-state light-emitting elements is expected to be proposed in the future. When the number of the arranged solid-state light-emitting elements serving as light-emitting portions and heat sources increases as above, the calorific value increases by the increased solid-state light-emitting elements. In the case as above, it is obvious that a higher cooling efficiency is demanded for the cooling apparatus applied in the light source apparatus for endoscope.

SUMMARY OF THE INVENTION

According to one aspect of the present invention, there is provided a light source apparatus for endoscope, including: a housing including an intake port; a first heat radiating portion provided in the housing, connected to a first light source configured to generate heat, and cooled when gas taken in from the intake port passes through the first heat radiating portion; a third heat radiating portion provided in the housing, connected to a third light source configured to generate heat, and cooled when gas taken in from the intake port passes through the third heat radiating portion; and a second heat radiating portion including a lower necessary cooling amount than the first heat radiating portion and the third heat radiating portion, provided in the housing, connected to a second light source configured to generate heat, provided in a flow path in which a flow path of the gas that passes through the first heat radiating portion and a flow path of the gas that passes through the third heat radiating portion are merged together, and cooled when merged gas merged on a merged flow path passes through the second heat radiating portion.

DETAILED DESCRIPTION OF THE PREFERRED EMBODIMENT(S)

Figure 1:
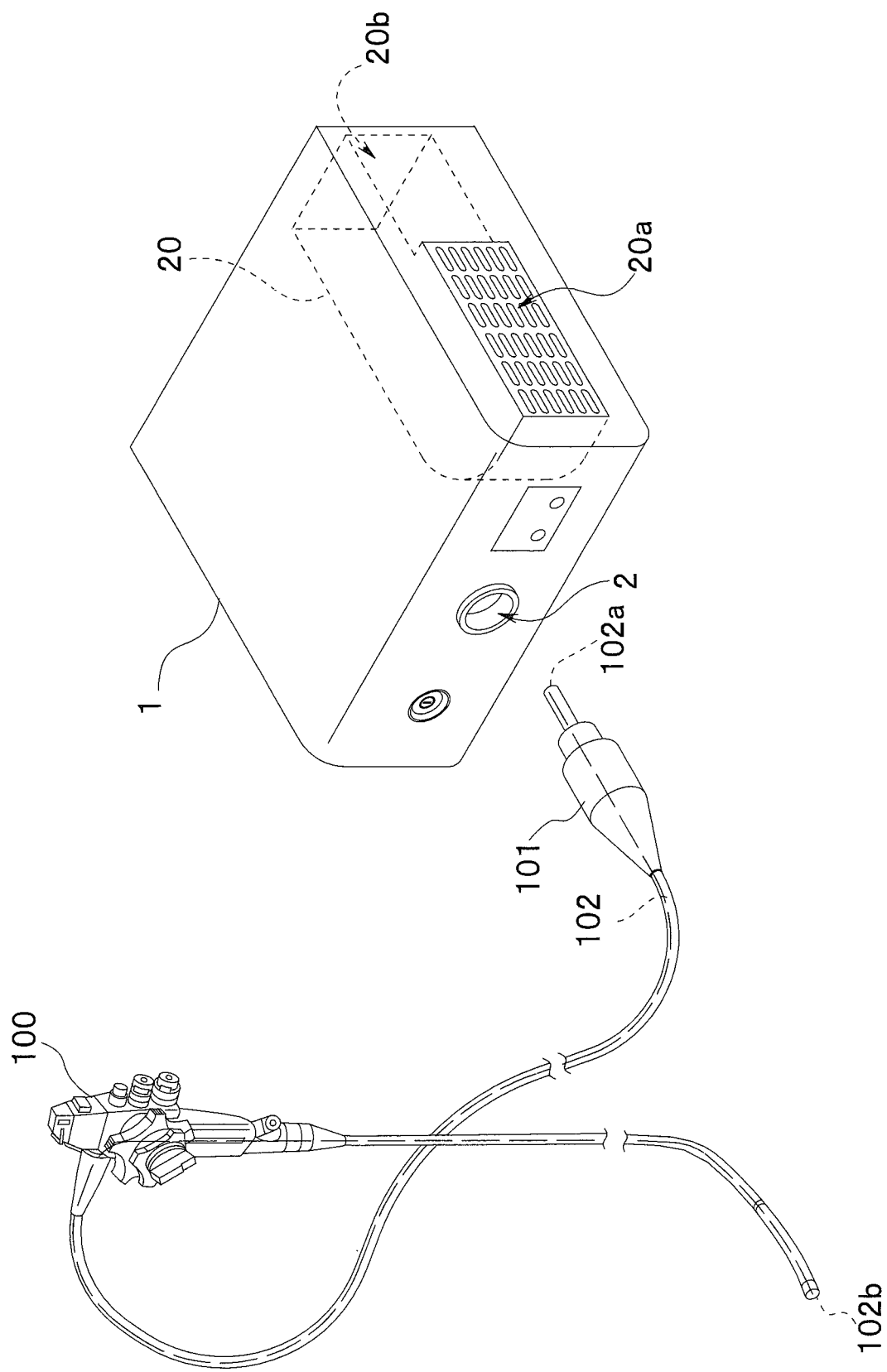
FIG. 1 is an entire configuration view illustrating an overview of an endoscope system to which a light source apparatus for endoscope of a first embodiment of the present invention is applied.

The present invention is described below by embodiments illustrated in the drawings. The respective drawings used in the description below are schematically illustrated, and dimensional relationships, scales, and the like of respective members may be illustrated in a manner in which the dimensions, the scales, and the like differ for every component in order to illustrate the respective components at sizes that can be recognized in the drawings. Therefore, the present invention is not limited to the illustrated forms in terms of number of the components, shapes of the components, size ratio among the components, relative positional relationship among the components, and the like illustrated in the respective drawings.

[First Embodiment]

A light source apparatus for endoscope 1 of this embodiment is an apparatus configured to generate and emit illumination light for illuminating a target that is observed with use of an endoscope 100. The light source apparatus for endoscope 1 includes a housing that has a substantially rectangular parallelepiped shape, and various types of components are included in the housing.

First, a schematic configuration of the light source apparatus for endoscope 1 of this embodiment and an endoscope system including an endoscope to which the light source apparatus for endoscope 1 is applied is described below mainly with reference to FIG. 1. FIG. 1 is an entire configuration view illustrating an overview of the endoscope system to which the light source apparatus for endoscope of this embodiment is applied.

An endoscope 100 is an apparatus configured to pick up an image of a section that is observed in a subject or an object such as a living body, and a structure, and display and output an image based on acquired image pickup data with use of a display apparatus (not shown). Note that the configuration of the endoscope 100 itself is well known, and a description of the endoscope 100 is omitted with the consideration that an endoscope similar to a conventional widespread endoscope is applied.

As illustrated in FIG. 1, the light source apparatus for endoscope 1 used by being connected to the endoscope 100 has a connector portion 2, which is on a front surface of the housing and serves as a connecting portion to which a plug portion 101 provided on the endoscope 100 is connected. One end 102a of an optical fiber cable 102 inserted into the endoscope 100 is arranged in the plug portion 101. Light emitted from the light source apparatus for endoscope 1 toward the one end 102a of the optical fiber cable 102 is transmitted via the optical fiber cable 102, emitted forward from the other end 102b of the optical fiber cable 102 provided on a distal end portion of the endoscope 100, and illuminates the target that is observed.

As described below, the light source apparatus for endoscope 1 includes a plurality of solid-state light-emitting elements (not shown in FIG. 1) therein, and is configured so that a light beam formed by bundling up light emitted from each of the solid-state light-emitting elements is emitted toward the one end 102a of the optical fiber cable 102 of the plug portion 101 connected to the connector portion 2.

The light source apparatus for endoscope 1 includes a cooling apparatus 20 configured to cool the plurality of solid-state light-emitting elements (not shown in FIG. 1). In the housing of the light source apparatus for endoscope 1, an intake port 20a serving as an opening portion for introducing air serving as a cooling medium to be caused to pass through the cooling apparatus 20 arranged in the housing into the housing, and an exhaust port 20b serving as an opening portion for discharging the air in the housing to the outside of the housing are provided. The intake port 20a is formed in one side surface of the housing of the light source apparatus for endoscope 1. In addition, the exhaust port 20b is formed in a second side surface (a rear surface in this embodiment) adjacent to the side surface in which the intake port 20a is formed in the housing of the light source apparatus for endoscope 1. Further, in the housing of the light source apparatus for endoscope 1, a tubular section connecting the intake port 20a and the exhaust port 20b with each other is referred to as a flow path through which the air serving as a cooling medium passes. The flow path is formed so as to pass through the cooling apparatus 20 in the housing of the light source apparatus for endoscope 1 (described in detail below).

Note that, in this embodiment, the intake port 20a is provided in one side surface of the light source apparatus for endoscope 1 and the exhaust port 20b is provided in the rear surface, that is, the second side surface adjacent to the one side surface as illustrated in FIG. 1. However, the sections in which the intake port 20a and the exhaust port 20b are provided are not limited to the examples in this embodiment. That is, the intake port 20a and the exhaust port 20b only need to be provided on any one of a front surface, a rear surface, a top surface, a bottom surface, the top surface, and both side surfaces of the housing of the light source apparatus for endoscope 1. In addition, the intake port 20a and the exhaust port 20b may be provided on the same surface of the housing of the light source apparatus for endoscope 1.

Note that, in the case as above, the front surface of the housing of the light source apparatus for endoscope 1 is a surface in which the connector portion 2 is provided. The rear surface of the housing is a surface opposed to the front surface. In addition, two surfaces adjacent to the front surface and the rear surface are referred to as the side surfaces. Further, a surface located on a lower-surface side when the housing of the light source apparatus for endoscope 1 is installed on a predetermined plane in a normal state (a state illustrated in FIG. 1) is referred to as the bottom surface, and a surface opposed to the bottom surface is referred to as the top surface.

Figure 2:
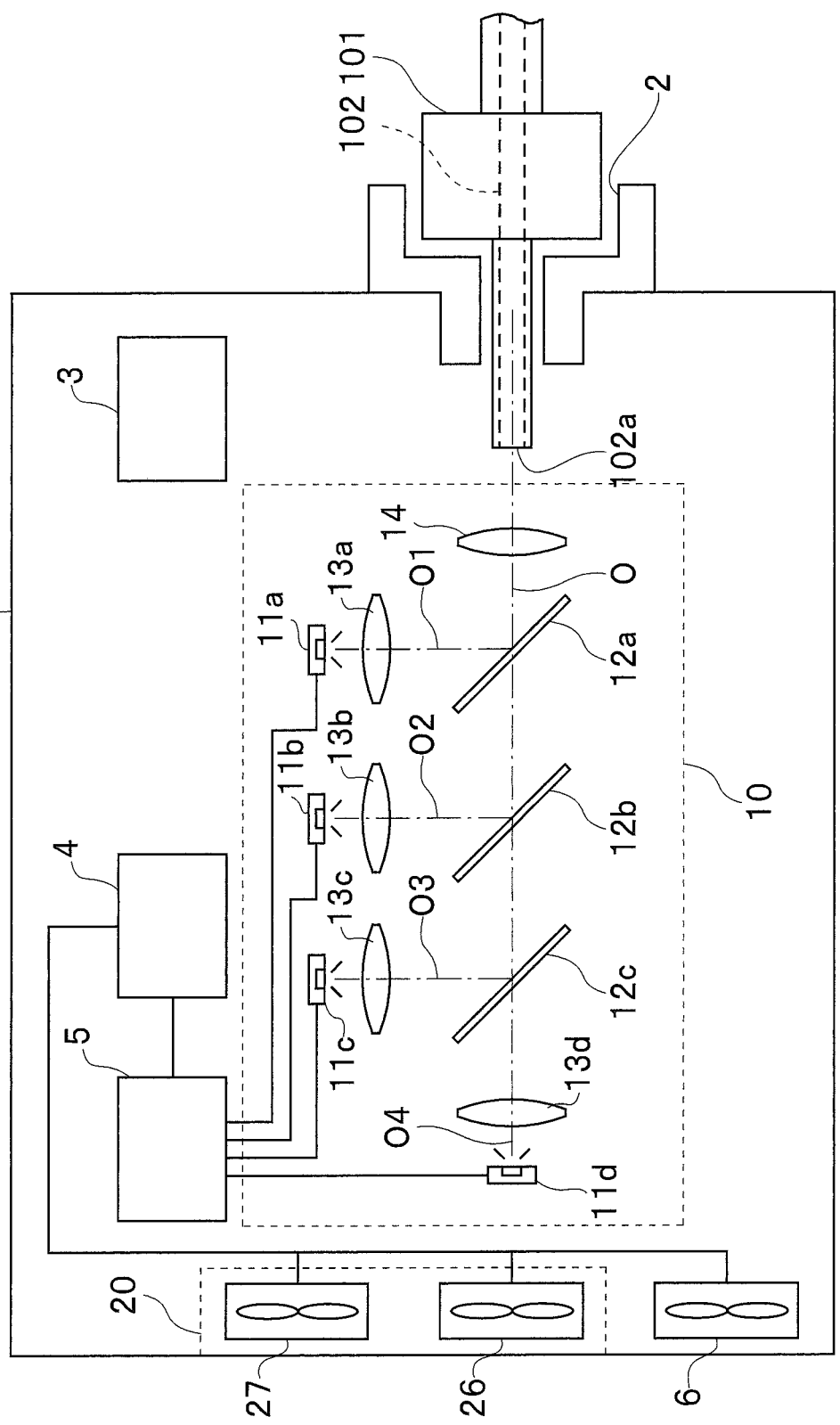
FIG. 2 is a block configuration diagram illustrating an overview of main parts of an internal configuration of the light source apparatus for endoscope of the first embodiment of the present invention.

Next, an overview of an internal configuration of the light source apparatus for endoscope 1 of this embodiment is described below with reference to FIG. 2. FIG. 2 is a block configuration diagram illustrating an overview of main parts of the internal configuration of the light source apparatus for endoscope 1 of this embodiment. Note that only main configurations of electrical components and optical components in the light source apparatus for endoscope 1 are illustrated in FIG. 2.

As illustrated in FIG. 2, the light source apparatus for endoscope 1 of this embodiment includes an illumination light emission portion 10, a power source portion 3, a control portion 4, a light source driving portion 5, a housing interior cooling fan 6, and light source cooling fans 26 and 27 configuring a part of the cooling apparatus 20. Note that a heat radiating portion (heat sink), a heat conducting portion (heat pipe), and the like out of the components configuring the cooling apparatus 20 are not illustrated in FIG. 2. The detailed configuration of the cooling apparatus 20 is described below.

The power source portion 3 is a power supply portion configured to supply power for driving each configuration unit of the light source apparatus for endoscope 1.

The control portion 4 is an apparatus configured to control operation of the light source apparatus for endoscope 1 on the basis of a predetermined program. Therefore, the control portion 4 includes a central processing unit (CPU), a storage (RAM; random access memory), an auxiliary storage, and an input-output device, for example.

The light source driving portion 5 is a configuration portion including an electric circuit configured to cause illumination light to be emitted by driving the illumination light emission portion 10 (the solid-state light-emitting elements; described below) in accordance with an instruction signal from the control portion 4.

The illumination light emission portion 10 includes the plurality of solid-state light-emitting elements. In this embodiment, an example in which the number of the plurality of solid-state light-emitting elements is four is described. Laser diodes, light emitting diodes (LEDs), or the like configured to emit light in predetermined wavelength ranges focused on different wavelengths are applied to the plurality of respective solid-state light-emitting elements, for example. Specifically, the plurality of solid-state light-emitting elements are a first solid-state light-emitting element 11a including a red LED, a second solid-state light-emitting element 11b including a green LED, a third solid-state light-emitting element 11c including a blue LED, and a fourth solid-state light-emitting element 11d including a violet LED, for example. Note that light colors (wavelengths) emitted by the respective solid-state light-emitting elements are not limited to the light colors above.

The plurality of solid-state light-emitting elements are electrically connected to the light source driving portion 5. As a result, the plurality of solid-state light-emitting elements are driven and controlled by the light source driving portion 5. That is, on-off control of light emission of the plurality of solid-state light-emitting elements is conducted by an instruction signal outputted from the light source driving portion 5. In addition, the plurality of solid-state light-emitting elements change light intensity to be emitted in accordance with the instruction signal outputted from the light source driving portion 5.

The respective light beams emitted from the plurality of (four) solid-state light-emitting elements (11a, 11b, 11c, and 11d) are respectively turned into parallel light by a plurality of corresponding collimator lenses (13a, 13b, 13c, and 13d), and is then guided to a condensing lens 14 by dichroic mirrors (12a, 12b, and 12c). The plurality of collimator lenses (13a, 13b, 13c, and 13d), the dichroic mirrors (12a, 12b, and 12c), and the condensing lens 14 are herein optical members configured to guide the light emitted from the plurality of solid-state light-emitting elements (11a, 11 b, 11c, and 11d; light sources) to the connector portion 2 serving as a connecting portion.

The condensing lens 14 serves a function of collecting the light emitted from the plurality of (four) solid-state light-emitting elements into the one end 102a of the optical fiber cable 102 of the plug portion 101 connected to the connector portion 2.

That is, in this embodiment, when an axis passing through a center of the condensing lens 14 is referred to as an optical axis O, one solid-state light-emitting element 11d is arranged on the optical axis O and the other three solid-state light-emitting elements (11a, 11b, and 11c) are arranged in adjacent positions that are off the optical axis O in the illumination light emission portion 10 of the light source apparatus for endoscope 1. The optical axis O is herein a central axis of the light emitted from the illumination light emission portion 10.

In addition, when central axes of the light emitted from the plurality of (four) respective solid-state light-emitting elements (11a, 11b, 11c, and 11d) are denoted by reference characters O1, O2, O3, and O4, an axis indicated by reference character O4 is parallel to the optical axis O. In addition, each of the three corresponding solid-state light-emitting elements (11a, 11b, and 11c) is arranged so that the other three central axes (reference characters O1, O2, and O3) are orthogonal to the optical axis O.

That is, the other three solid-state light-emitting elements (11a, 11 b, and 11c) besides the solid-state light-emitting element 11d are arranged so that the axes indicated by reference characters O1, O2, and O3 are orthogonal to the optical axis O in the same plane including the optical axis O. In addition, in the same plane including the optical axis O, the other three solid-state light-emitting elements (11a, 11b, and 11c) are all arranged side by side on the same side with respect to the optical axis O (an upper position illustrated in FIG. 2) in a direction parallel to the optical axis O.

The plurality of collimator lenses (13a, 13b, 13c, and 13d) are respectively arranged in front of the plurality of solid-state light-emitting elements (11a, 11b, 11c, and 11d), that is, arranged on an optical path through which the emitted light passes. By the configuration as above, the light emitted from each of the solid-state light-emitting elements (11a, 11b, 11 c, and 11d) is transmitted and emitted as parallel light.

The plurality of dichroic mirrors (12a, 12b, and 12c) are respectively provided in front of three collimator lenses (13a, 13b, and 13c) out of the plurality of (four) collimator lenses (13a, 13b, 13c, and 13d), that is, provided on the optical path of the emitted light. The respective dichroic mirrors (12a, 12b, and 12c) are arranged along the optical axis O at predetermined intervals. Reflective surfaces of the respective dichroic mirrors (12a, 12b, and 12c) are orthogonal to the plane including the optical axis O and the central axes O1, O2, and O3, and each of the reflective surfaces is arranged on the plane so as to be tilted from the optical axis O by about 45 degrees. In the case as above, the reflective surfaces of the respective dichroic mirrors (12a, 12b, and 12c) are arranged to face the other three solid-state light-emitting elements (11a, 11b, and 11c) and the condensing lens 14. By the configuration as above, the respective reflective surfaces of the respective dichroic mirrors (12a, 12b, and 12c) reflect the emitted light from the other three solid-state light-emitting elements (11a, 11 b, and 11c) toward the condensing lens 14.

The reflective surface of the dichroic mirror 12a out of the plurality of dichroic mirrors reflects light in a predetermined wavelength band including a wavelength of the light emitted from the solid-state light-emitting element 11a and transmits light in other wavelength bands. In addition, the reflective surface of the dichroic mirror 12b reflects light in a predetermined wavelength band including a wavelength of the light emitted from the solid-state light-emitting element 11b, and transmits light in other wavelength bands. Further, the reflective surface of the dichroic mirror 12c reflects light in a predetermined wavelength band including a wavelength of the light emitted from the solid-state light-emitting element 11c, and transmits light in other wavelength bands. On the other hand, the respective dichroic mirrors (12a, 12b, and 12c) transmit light in a predetermined wavelength band including a wavelength of the light emitted from the solid-state light-emitting element 11d.

The parallel light, which is emitted from the plurality of solid-state light-emitting elements (11a, 11 b, and 11c) and emitted via the plurality of collimator lenses (13a, 13b, and 13c), is reflected by the dichroic mirrors 12a, 12b, and 12c and is combined with the parallel light, which is emitted from the solid-state light-emitting element 11d and emitted via the collimator lens 13d. The combined light enters the condensing lens 14.

In the illumination light emission portion 10 including the configuration as described above, the plurality of (four)

solid-state light-emitting elements (11a, 11b, 11 c, and 11d) are arranged so that the central axes of the light emitted from the respective solid-state light-emitting elements are located in the same plane. Further, the respective solid-state light-emitting elements (11a, 11b, 11c, and 11d) can be said to be arranged in order in a predetermined direction along the optical axis O. In addition, the plurality of (four) solid-state light-emitting elements (11a, 11 b, 11c, and 11d) are arranged so as not to overlap with each other in the direction orthogonal to the optical axis O.

Note that the number of the solid-state light-emitting elements included in the illumination light emission portion 10 is not limited to the abovementioned example (four), and only needs to be two or more, for example.

The housing interior cooling fan 6 is an electric fan configured to discharge air in the housing of the light source apparatus for endoscope 1 to the outside. The housing interior cooling fan 6 is driven and controlled by the control portion 4. That is, the control portion 4 performs control for changing a rotational speed of the housing interior cooling fan 6, for example, by driving and controlling the housing interior cooling fan 6. Note that the number of the housing interior cooling fan 6 is not limited to one, and a form in which a plurality of housing interior cooling fans 6 are provided is possible.

The light source cooling fans 26 and 27 are electric fans included in the cooling apparatus 20 described below. The light source cooling fans 26 and 27 are also driven and controlled by the control portion 4. That is, the control portion 4 performs control for changing rotational speeds of the light source cooling fans 26 and 27, for example, by driving and controlling the light source cooling fans 26 and 27. Note that the light source cooling fans are also not limited to the abovementioned example, and a form in which three or more light source cooling fans are provided is possible.

Figure 3:
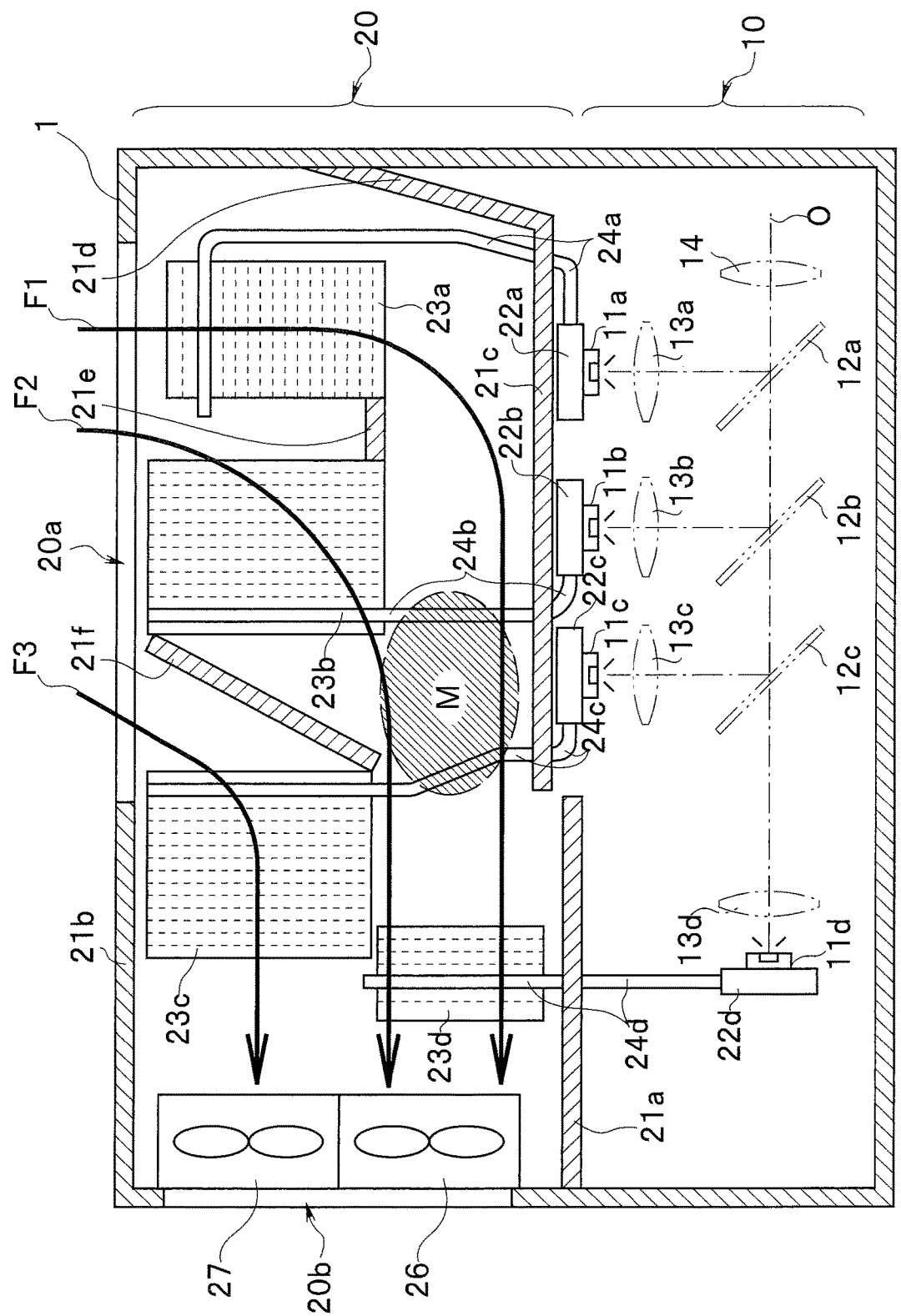
FIG. 3 is a schematic configuration diagram illustrating a configuration of a cooling apparatus of the light source apparatus for endoscope of the first embodiment of the present invention.

Next, a configuration of the cooling apparatus 20 in the light source apparatus for endoscope 1 of this embodiment is described below mainly with reference to FIG. 3. FIG. 3 is a schematic configuration diagram illustrating the configuration of the cooling apparatus 20 of the light source apparatus for endoscope 1 of this embodiment.

As illustrated in FIG. 3, the cooling apparatus 20 is a configuration unit configured to cool the solid-state light-emitting elements (11a, 11 b, 11c, and 11d) serving as heat-generating portions out of the components of the illumination light emission portion 10. The cooling apparatus 20 includes a plurality of rectifier portions (21a, 21b, 21c, 21d, 21e, and 21f), a plurality of heat receiving portions (22a, 22b, 22c, and 22d), a plurality of heat sinks (23a, 23b, 23c, and 23d) serving as a plurality of heat radiating portions, a plurality of heat pipes (24a, 24b, 24c, and 24d) serving as a plurality of heat conducting portions, and the like.

In the housing in the light source apparatus for endoscope 1, a flow path through which gas (usually air; hereinafter simply referred to as air) serving as a cooling medium for cooling the plurality of solid-state light-emitting elements (11a, 11b, 11c, and 11d) serving as heating elements passes is formed. The flow path has a section extending in a direction along the optical axis O. That is, the flow path in the housing is formed in sections in which the cooling medium (air) flows along the arrangement direction of the plurality of solid-state light-emitting elements (11a, 11b, 11 c, and 11d). One end of the flow path is connected to the intake port 20a provided in one side surface of the housing and the other end of the flow path is connected to the exhaust port 20b provided in the second side surface of the housing. Further, in the flow path, the cooling medium (air) flows into the housing from the intake port 20a and flows so as to be discharged to the outside of the housing from the exhaust port 20b. That is, in the flow path, a section near the intake port 20a is an upstream side of the flow (flow path) of the air in the flow path and a section near the exhaust port 20b is a downstream side of the flow of the air.

The flow path in the housing of the light source apparatus for endoscope 1 of this embodiment extends in the vicinity of the respective rear surface sides of the three solid-state light-emitting elements (11a, 11b, and 11c) having central axes orthogonal to the optical axis O out of the plurality of solid-state light-emitting elements (11a, 11b, 11c, and 11d) along the arrangement direction of the respective solid-state light-emitting elements (11a, 11b, and 11c). The rear surfaces of the three solid-state light-emitting elements (11a, 11b, and 11c) herein are surfaces facing a direction opposite from emission surfaces of the light emitted from the respective solid-state light-emitting elements. By the configuration above, in the housing of the light source apparatus for endoscope 1, the three solid-state light-emitting elements (11a, 11 b, and 11c) are arranged between the flow path and the optical axis O.

In other words, the three solid-state light-emitting elements (11a, 11b, and 11c; the plurality of heat-generating portions) arranged along the optical axis O are arranged along the flow path side wall 21c at predetermined intervals. In the case as above, the respective solid-state light-emitting elements (11a, 11b, and 11c) are arranged in order from the upstream side of the flow path to the downstream side of the flow path in a direction (see an arrow F1) in which the air in the flow path flows.

In FIG. 3, directions in which the air flows are indicated by arrows F1, F2, and F3 as the flow path in the housing of the light source apparatus for endoscope 1. That is, the flow path in the housing of the light source apparatus for endoscope 1 of this embodiment is divided into three flow paths, that is, a first flow path through which the air flows in the arrow F1, a second flow path through which the air flows in the arrow F2, and a third flow path through which the air flows in the arrow F3.

Therefore, the partition plate 21e serving as a rectifier portion is arranged between the first flow path F1 and the second flow path F2. The two flow paths (the first flow path F1 and the second flow path F2) are formed by the partition plate 21e. Note that, in this embodiment, the first flow path F1 and the second flow path F2 are formed so as to be merged together in a predetermined region (a section indicated by a character M in FIG. 3) in the housing as illustrated in FIG. 3 (details are described below). In addition, the first flow path F1 is formed along the flow path side walls 21d, 21c, and 21a. Further, the second flow path F2 is formed along the first flow path F1 across the partition plate 21e, and the first flow path F1 and the second flow path F2 are merged together in a section (merging region M) in the middle of the flow path. Then, the first flow path F1 and the second flow path F2 form the same flow path on the downstream side of the flow path.

On the other hand, the partition plate 21f serving as a rectifier portion is arranged between the second flow path F2 and the third flow path F3. The two flow paths (the second flow path F2 and the third flow path F3) are formed by the partition plate 21f. That is, the third flow path F3 forms a flow path that is almost independent along the housing side wall 21b and the partition plate 21f. In other words, the partition plate 21f functions as a rectifier portion that divides the flow path of the air passing through the third heat sink 23c (a fourth heat radiating portion; described below) and the flow path of the air passing through the second heat sink 23b (a first heat radiating portion; described below) and the first heat sink 23a (a third heat radiating portion; described below) from each other.

As described above, the respective components configuring the cooling apparatus 20 are arranged in the flow paths formed in the housing.

That is, the plurality of heat receiving portions (22a, 22b, 22c, and 22d) are fixed to the respective rear surface sides of the plurality of solid-state light-emitting elements (11a, 11b, 11c, and 11d) so as to be in contact with the respective rear surface sides. The plurality of heat receiving portions (22a, 22b, 22c, and 22d) are heat conduction members provided to transmit the heat generation of the plurality of solid-state light-emitting elements (11a, 11b, 11c, and 11d). The plurality of heat receiving portions include the first heat receiving portion 22a provided on the rear surface side of the first solid-state light-emitting element 11a and configured to conduct the heat generation of the first solid-state light-emitting element 11a, the second heat receiving portion 22b provided on the rear surface side of the second solid-state light-emitting element 11b and configured to conduct the heat generation of the second solid-state light-emitting element 11b, the third heat receiving portion 22c provided on the rear surface side of the third solid-state light-emitting element 11c and configured to conduct the heat generation of the third solid-state light-emitting element 11c, and the fourth heat receiving portion 22d provided on the rear surface side of the fourth solid-state light-emitting element 11d and configured to conduct the heat generation of the fourth solid-state light-emitting element 11d.

Note that the plurality of heat receiving portions and the plurality of solid-state light-emitting elements may be arranged in a form in abutment against each other, but a form in which a member having a high heat transfer coefficient is sandwiched between the plurality of heat receiving portions and the plurality of solid-state light-emitting elements is also possible as another form, for example. In addition, an example in which the plurality of respective heat receiving portions are arranged on the respective rear surface sides of the plurality of solid-state light-emitting elements is described in this embodiment, but the present invention is not limited to the abovementioned form. The arrangement and shapes of the heat receiving portions with respect to the solid-state light-emitting element only need to be a form in which the heat receiving portions do not block the light emission surfaces of the solid-state light-emitting elements, and any kind of shape may be allowed.

The plurality of heat sinks (23a, 23b, 23c, and 23d) serving as a plurality of heat radiating portions are respectively arranged in predetermined positions in the flow path. The cooling apparatus 20 in this embodiment includes the same number of heat sinks as the plurality of heat receiving portions (that is, the plurality of solid-state light-emitting elements), that is, four heat sinks (23a, 23b, 23c, and 23d). The plurality of heat sinks include the first heat sink 23a arranged in the vicinity of the intake port 20a in the first flow path F1, the second heat sink 23b arranged in the vicinity of the intake port 20a in the second flow path F2, the third heat sink 23c arranged in the vicinity of the intake port 20a in the third flow path F3, and the fourth heat sink 23d arranged on a side downstream of the merging region M in the first flow path F1 and the second flow path F2. In the case as above, the second heat sink 23b is the first heat radiating portion, which is arranged in the flow path through which air taken in from the intake port 20a passes and which is cooled by the air.

In addition, the fourth heat sink 23d is a second heat radiating portion, which is arranged in the flow path of the air passing through the second heat sink 23b (first heat radiating portion) and which is cooled when the air that passes through the second heat sink 23b (first heat radiating portion) passes through the fourth heat sink 23d.

Further, the first heat sink 23a is the third heat radiating portion, which is arranged in the flow path through which the air taken in from the intake port 20a passes and which is cooled by the air.

In addition, the third heat sink 23c is the fourth heat radiating portion, which is arranged in the flow path through which the air taken in from the intake port 20a passes and which is cooled by the air. Further, the flow path (the second flow path F2) of the gas that has passed through the second heat sink 23b (first heat radiating portion) and the flow path (the first flow path F1) of the gas that has passed through the first heat sink 23a (third heat radiating portion) are merged together in the merging region M in the housing.

In addition, the sizes the plurality of heat sinks are formed to be different from each other in the light source apparatus for endoscope 1 in this embodiment as illustrated in FIG. 3. The size of the heat sink is herein indicated by a cross-sectional area through which the air serving as a cooling medium passes and a surface area through which the air passes. The size of the heat sink defines a cooling capacity.

The plurality of solid-state light-emitting elements serving as a plurality of heat-generating portions in the light source apparatus for endoscope 1 have calorific values and maximum temperatures at which operation is guaranteed that differ from each other in accordance with the wavelength of the light to be emitted. Therefore, the cooling apparatus 20 that prevents the upsizing of the apparatus while obtaining a more-efficient cooling effect can be provided by setting the cooling capacity of the heat radiating portions (heat sinks) in accordance with a ratio of the calorific value to the maximum temperature at which operation is guaranteed for each solid-state light-emitting element.

The cooling capacity of the heat radiating portions (heat sinks) in the cooling apparatus 20 can be defined by the size of the cross-sectional area and the surface area through which the air serving as a cooling medium passes. That is, the cooling capacity can be increased as the cross-sectional area and the surface area though which the air passes in the heat radiating portions (heat sinks) increase.

Thus, in the light source apparatus for endoscope 1 of this embodiment, the respective sizes of the four heat sinks are defined in accordance with the degree of cooling necessary in the plurality of solid-state light-emitting elements (11a, 11b, 11c, and 11d) that are applied. More specifically, for example, in this embodiment, three heat radiating portions arranged on the upstream side of the flow path (in the vicinity of the intake port 20a), that is, the first heat sink 23a (third heat radiating portion), the second heat sink 23b (first heat radiating portion), and the third heat sink 23c (fourth heat radiating portion) out of the plurality of heat sinks (heat radiating portions) are connected to the solid-state light-emitting elements having a relatively high ratio of the calorific value to the maximum temperature at which operation is guaranteed, that is, the first solid-state light-emitting element 11a, the second solid-state light-emitting element 11b, and the third solid-state light-emitting element 11c, respectively. Note that the second heat sink 23b (first heat radiating portion) is connected to the second solid-state light-emitting element 11b (first light source) provided in the housing. Further, out of the heat sinks, a heat sink having a higher cooling capacity than the second heat sink 23b (first heat radiating portion) and the first heat sink 23a (third heat radiating portion) is applied to the third heat sink 23c (fourth heat radiating portion). The configuration is a measure against the ratio of the calorific value to the maximum temperature at which operation is guaranteed of the third solid-state light-emitting element 11c corresponding to the third heat sink 23c (fourth heat radiating portion) being the highest.

On the other hand, the solid-state light-emitting element having a relatively low ratio of the calorific value to the maximum temperature at which operation is guaranteed, that is, the fourth solid-state light-emitting element 11d is connected to the fourth heat sink 23d arranged on the downstream side of the merging region M. The fourth solid-state light-emitting element 11d is herein a second light source provided in the housing, connected to the fourth heat sink 23d (second heat radiating portion), having a ratio of the calorific value to the maximum temperature at which operation is guaranteed that is lower than the second solid-state light-emitting element 11b (first light source), and arranged in a position closer to the rear surface than the second solid-state light-emitting element 11b (first light source) in the housing.

Further, the plurality of heat receiving portions and the plurality of heat radiating portions (heat sinks) are connected with each other by the plurality of heat pipes (24a, 24b, 24c, and 24d) serving as a plurality of heat conducting portions, respectively. That is, the plurality of heat pipes include the first heat pipe 24a connecting the first heat receiving portion 22a and the first heat sink 23a with each other, the second heat pipe 24b connecting the second heat receiving portion 22b and the second heat sink 23b with each other, the third heat pipe 24c connecting the third heat receiving portion 22c and the third heat sink 23c with each other, and the fourth heat pipe 24d connecting the fourth heat receiving portion 22d and the fourth heat sink 23d with each other.

Note that the heat receiving portions and the heat sinks may directly come into contact with each other without the intermediary of the heat pipes serving as heat conducting portions. The heat sinks only need to be arranged in sections proximate to the heat receiving portions in order to employ the configuration. Therefore, the heat pipes can be unnecessary in the connection between the first to fourth heat receiving portions and the first to fourth heat sinks described above depending on the arrangement configuration. Note that the form of the plurality of heat conducting portions is not limited to the form of the heat pipes described above, and the plurality of heat conducting portions only need to be members capable of realizing efficient heat conduction.

The four heat pipes (24a, 24b, 24c, and 24d) horizontally extend from the solid-state light-emitting elements serving as heat-generating portions and are respectively connected to the corresponding heat sinks. As a result, the respective heat pipes are arranged in the flow path so as to be substantially orthogonal to the flow direction of the cooling medium (air) in the flow path, that is, so as to cross the flow of the air in the flow path.

As described above, the light source apparatus for endoscope 1 of this embodiment includes two light source cooling fans 26 and 27 (see FIG. 2 and FIG. 3) and the housing interior cooling fan 6 (see FIG. 2; not shown in FIG. 3). Now, out of the two light source cooling fans 26 and 27, one is an electric fan provided to cause the cooling medium (air) to flow to the first flow path F1 and the second flow path F2 at a predetermined flow rate. Further, the other is an electric fan provided to cause the cooling medium (air) to flow to the third flow path F3 at a predetermined flow rate.

In this embodiment, an example in which the two light source cooling fans 26 and 27 are arranged in the vicinity of the exhaust port 20b, that is, an end portion on the downstream side of the flow path is described. In addition, axial fans are applied as the form of the two light source cooling fans 26 and 27, for example.

The two light source cooling fans 26 and 27 only need to include a function of causing the cooling medium (air) to flow from the intake port 20a toward the exhaust port 20b at a predetermined flow rate in the housing in the light source apparatus for endoscope 1, and the form, the number, the arrange positions, and the like of the light source cooling fans 26 and 27 are not particularly limited to the example above. For example, a form in which at least one of the light source cooling fans 26 and 27 is arranged in the vicinity of the intake port 20a is possible. In addition, at least one of the light source cooling fans 26 and 27 may be a centrifugal fan (blower fan).

In the cooling apparatus 20 configured as above, the air flows in the flow path (the first flow path F1, the second flow path F2, and the third flow path F3) at a predetermined flow rate by operating the light source cooling fans 26 and 27. In the flow path, the plurality of heat sinks (23a, 23b, 23c, and 23d) are arranged in the respective predetermined sections. Therefore, the cooling medium (air) flowing in the flow path passes through the respective heat sinks. Now, the plurality of heat sinks are connected to the plurality of solid-state light-emitting elements (11a, 11b, 11c, and 11d) via the plurality of heat pipes (24a, 24b, 24c, and 24d; the heat conducting portions) and the plurality of heat receiving portions (22a, 22b, 22c, and 22d). Therefore, by the configuration, heat generated from the plurality of solid-state light-emitting elements (11a, 11b, 11c, and 11d) can be released by the plurality of heat sinks. That is, the cooling apparatus 20 cools the plurality of solid-state light-emitting elements (11a, 11b, 11c, and 11d).

Now, the light source apparatus for endoscope 1 of this embodiment includes the second heat sink 23b (first heat radiating portion) arranged in the flow path through which the air taken in from the intake port 20a provided in the housing passes and configured to cool the air, the fourth heat sink 23d (second heat radiating portion) arranged in the flow path of the air that has passed through the second heat sink 23b (first heat radiating portion) and configured to cool the air when the air that has passed through the second heat sink 23b (first heat radiating portion) passes through the fourth heat sink 23d, and the first heat sink 23a (third heat radiating portion) arranged in the flow path through which the air taken in from the intake port 20a passes and configured to cool the air are included in the flow path through which the cooling medium (air) flows, and the flow path (F2) of the gas that has passed through the second heat sink 23b (first heat radiating portion) and the flow path (F2) of the gas that has passed through the first heat sink 23a (third heat radiating portion) are merged together.

In addition, the third heat sink 23c (fourth heat radiating portion) has a higher cooling capacity than the second heat sink 23b (the first heat radiating portion) and the first heat sink 23a (third heat radiating portion). The third heat sink 23c (fourth heat radiating portion) is arranged in the flow path through which the air taken in from the intake port 20a provided in the housing passes, configured to cool the air, and includes the partition plate 21f that divides the flow path of the air passing through the third heat sink 23c (fourth heat radiating portion) and the flow path of the air passing through the second heat sink 23b (first heat radiating portion) and the first heat sink 23a (third heat radiating portion).

As described above, according to the abovementioned first embodiment, in the flow path through which the cooling medium (air) flows, the heat sink corresponding to the solid-state light-emitting element having a relatively low degree of cooling necessary, that is, the fourth heat sink 23d (second heat radiating portion) is arranged on the downstream side of the flow path and the flow path is configured so that the air that has passed through the second heat sink 23b (first heat radiating portion) and the first heat sink 23a (third heat radiating portion) out of the heat sinks corresponding to the solid-state light-emitting elements having a relatively high degree of cooling necessary are merged together. As a result, the air that has passed through both heat sinks (23b and 23a) pass through the fourth heat sink 23d (second heat radiating portion). Further, the third heat sink 23c (fourth heat radiating portion) corresponding to the solid-state light-emitting element having the highest degree of cooling necessary is arranged in an independent flow path.

By the configuration as above, larger cross-sectional areas for the flow paths passing through the respective heat radiating portions corresponding to the respective solid-state light-emitting elements can be ensured without finely dividing the flow path in correspondence to the plurality of heat sources. Therefore, the light source apparatus for endoscope 1 of this embodiment can contribute to the further enhancement of the cooling capacity while preventing the upsizing of the apparatus by effectively using the limited internal space in the housing.

[Second Embodiment]

Figure 4:
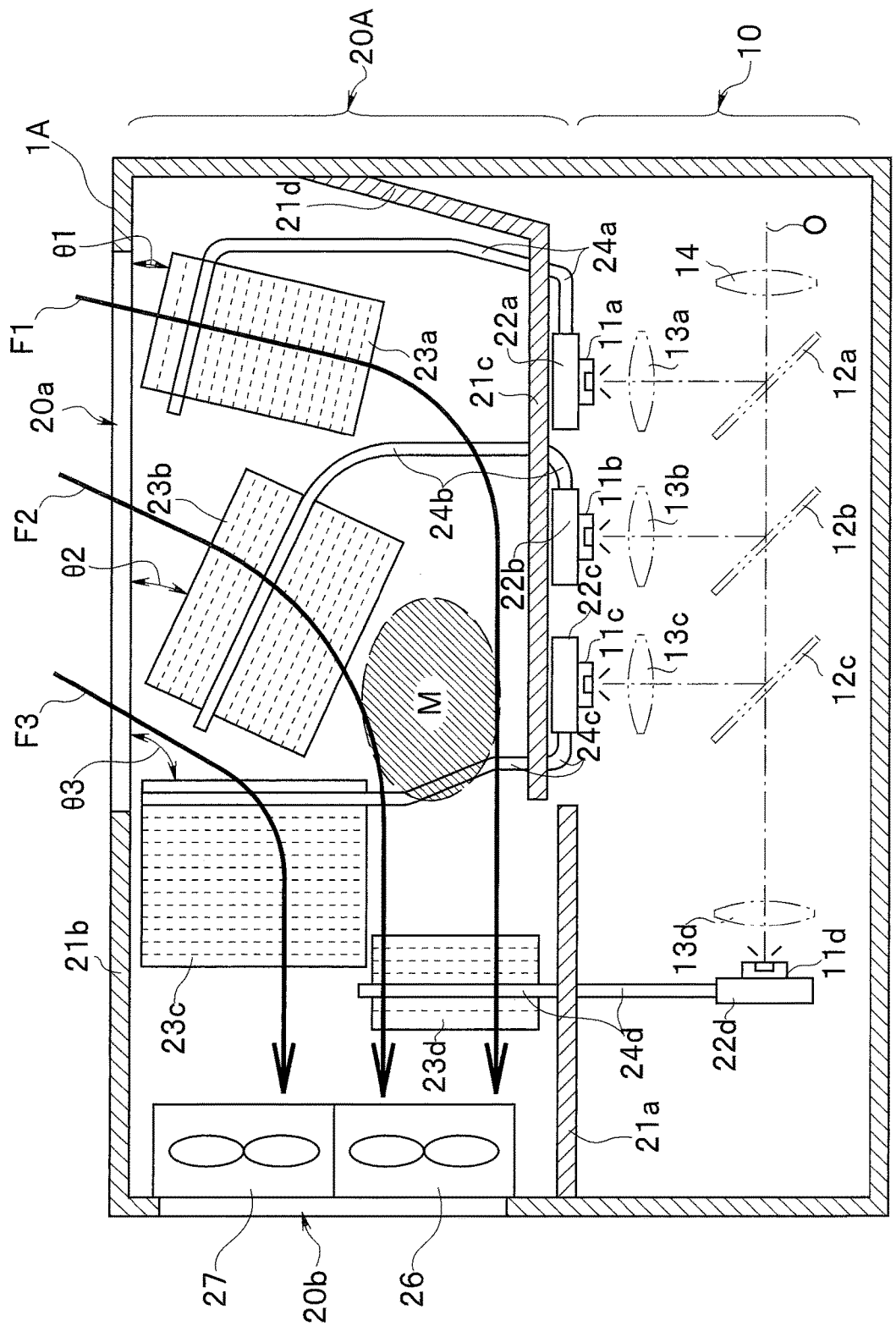
FIG. 4 is a schematic configuration diagram illustrating a configuration of a cooling apparatus of a light source apparatus for endoscope of a second embodiment of the present invention.

Next, a light source apparatus for endoscope of a second embodiment of the present invention is described with reference to FIG. 4. FIG. 4 is a schematic configuration diagram illustrating a configuration of a cooling apparatus of a light source apparatus for endoscope of the second embodiment of the present invention.

The basic configuration of this embodiment is substantially similar to the basic configuration of the first embodiment described above. In this embodiment, only a configuration of a cooling apparatus 20A arranged in a housing of a light source apparatus for endoscope 1A is slightly different.

That is, in the cooling apparatus 20A of the light source apparatus for endoscope 1A of this embodiment, three heat radiating portions arranged on the upstream side of the flow path (in the vicinity of the intake port 20a), that is, the first heat sink 23a (third heat radiating portion), the second heat sink 23b (first heat radiating portion), and the third heat sink 23c (fourth heat radiating portion) out of a plurality of heat sinks (heat radiating portions) are arranged so that surfaces of the respective heat sinks through which air passes are tilted by predetermined inclination angles (see characters θ1, θ2, and θ3 in FIG. 4) with respect to an intake surface (one side surface of the housing) of the intake port 20a in the housing.

In the case as above, $$0° < \theta \leq 90°$$

is satisfied where the character θ collectively represents the inclination angles (θ1, θ2, and θ3). In addition, the inclination angle θ1 out of the inclination angles (θ1, θ2, and θ3) of the respective heat sinks is an inclination angle of an air passing surface of the first heat sink 23a (third heat radiating portion) with respect to the intake surface. Similarly, the inclination angle θ2 is an inclination angle of an air passing surface of the second heat sink 23b (first heat radiating portion) with respect to the intake surface. Further, the inclination angle θ3 is similarly an inclination angle of an air passing surface of the third heat sink 23c (fourth heat radiating portion) with respect to the intake surface.

Further, it is desired that each of the inclination angles be set so that a heat sink arranged on a side far from the exhaust port 20b has an air passing surface of which inclination angle with respect to the intake surface is shallower (smaller) than an inclination angle of an air passing surface of a heat sink arranged on the side near the exhaust port 20b with respect to the intake surface, for example. Similarly, it is desired that a heat sink arranged on a side near the exhaust port 20b be set to have an air passing surface of which inclination angle with respect to the intake surface is the steepest (largest). In this embodiment, the inclination angles of the air passing surfaces of the respective heat sinks with respect to the intake surface are set so that θ1<θ2<θ3 is satisfied, for example, as illustrated in FIG. 4.

The reason the arrangement configuration as above is employed is as follows. That is, the housing of the light source apparatus for endoscope 1A of this embodiment is configured to discharge air taken in from the intake port 20a on one side surface of the housing to the exhaust port 20b of a second side surface (rear surface) adjacent to the side surface. In the housing having the configuration as above, a smooth flow of a cooling medium (air) flowing through the respective flow paths (the first flow path F1, the second flow path F2, and the third flow path F3) is ensured by tilting the inclination angles of the air passing surfaces of the respective heat sinks (23a, 23b, and 23c) with respect to the intake surface. Other configurations are similar to the configurations of the first embodiment described above.

According to this embodiment, it becomes easier to cause the cooling medium (air) to flow through the respective flow paths (the first flow path F1, the second flow path F2, and the third flow path F3) more smoothly by employing the configuration as above. In addition, in the merging region M of the first flow path F1 and the second flow path F2, the mixing between the air that has passed through the first heat sink 23a and the air that has passed through the second heat sink 23b can be easier. Therefore, a temperature distribution of the air passing through the fourth heat sink 23d that is a heat sink (heat radiating portion) on the downstream side of the flow path can be reduced. As a result, the cooling effect in the cooling apparatus 20 can be increased more.

Note that the present invention is not limited to the embodiments described above, and it goes without saying that various modifications and applications may be made without departing from the gist of the present invention. Further, the abovementioned embodiments include the invention in various stages, and various inventions may be extracted by combining the plurality of disclosed components as appropriate. For example, even if some components are erased from all the components described in one embodiment, the configuration in which the components are erased can be extracted as the invention when the technical problem can be solved and the effect of the invention can be obtained. Further, components in different embodiments may be combined as appropriate. The present invention is not limited by a particular embodiment of the present invention besides being limited by the attached claims.

The present invention can be applied not only to an endoscope control apparatus in a medical field but also to an endoscope control apparatus in an industrial field.

What is claimed is:

1. A light source apparatus for endoscope, comprising:
   a housing including an intake port;
   a first heat sink provided in the housing, the first heat sink being connected to a first light source configured to generate heat, the first heat sink being cooled when an ambient air is directly taken in from the intake port to pass through the first heat sink;
   a third heat sink provided in the housing, the third heat sink being connected to a third light source configured to generate heat, the third heat sink being cooled when the ambient air is directly taken in from the intake port to pass through the third heat sink; and
   a second heat sink provided in the housing, the second heat sink requiring a lower necessary cooling amount than the first heat sink and the third heat sink, the second heat sink being connected to a second light source configured to generate heat, the second heat sink being provided in a flow path in which a flow path of the ambient air that passes through the first heat sink and a flow path of the ambient air that passes through the third heat sink are merged together into a merged flow path, the second heat sink being cooled when the merged flow path passes through the second heat sink.

2. The light source apparatus for endoscope according to claim 1, further comprising:
   a fourth heat sink, which requires a higher cooling capacity than the first heat sink and the third heat sink, the fourth heat sink being cooled when the ambient air directly taken in from the intake port provided in the housing passes through the fourth heat sink; and
   a wall that divides a flow path of the ambient air that passes through the fourth heat sink from each of the flow paths of the ambient air that passes through the first heat sink and the third heat sink.

3. The light source apparatus for endoscope according to claim 1, wherein:
   the housing is formed so that the intake port is provided in one side surface and an exhaust port is provided in a second side surface adjacent to the one side surface; and
   the first heat sink and the third heat sink are arranged so that each ambient air passing surface is tilted with respect to an intake surface of the intake port along the flow paths of the ambient air from the intake port toward the exhaust port.

4. The light source apparatus for endoscope according to claim 3, further comprising:
   a first heat pipe, which extends in a direction perpendicular to a direction in which the ambient air passing through the first heat sink passes and which is configured to conduct heat from the first light source to the first heat sink by being connected to the first heat sink; and
   a second heat pipe, which extends in a direction perpendicular to a direction in which the ambient air passing through the third heat sink passes and which is configured to conduct heat from the third light source to the third heat sink by being connected to the third heat sink.

5. The light source apparatus for endoscope according to claim 3, wherein one of the first heat sink and the third heat sink that is arranged in a position that is nearest to the exhaust port includes an ambient air passing surface inclination angle with respect to an opening surface of the intake port of the housing that is larger than an ambient air passing surface inclination angle of the other of the first heat sink and the third heat sink.

6. The light source apparatus for endoscope according to claim 1, wherein the housing includes:
   the intake port in one side surface;
   an exhaust port that exhausts the ambient air that passes through the second heat sink in a rear surface; and
   a connector to which an endoscope is connected on a front surface,
   the light source apparatus for endoscope comprising one or more optical members configured to guide light emitted from the first light source and light emitted from the second light source to the connector.

7. The light source apparatus for endoscope according to claim 6, wherein the second light source is a light source including a lower ratio of a calorific value of the light source to a maximum temperature of the light source at which operation is guaranteed than the first light source.

* * * * *